United States Patent
Mahmoudi

(10) Patent No.: US 11,406,740 B2
(45) Date of Patent: Aug. 9, 2022

(54) NANOFIBROUS SCAFFOLDS TO HEAL CHRONIC SKIN WOUNDS

(71) Applicant: The Brigham and Women's Hospital, Inc., Boston, MA (US)

(72) Inventor: Morteza Mahmoudi, Chestnut Hill, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 36 days.

(21) Appl. No.: 17/055,786

(22) PCT Filed: May 16, 2019

(86) PCT No.: PCT/US2019/032683
§ 371 (c)(1),
(2) Date: Nov. 16, 2020

(87) PCT Pub. No.: WO2019/222511
PCT Pub. Date: Nov. 21, 2019

(65) Prior Publication Data
US 2021/0106727 A1    Apr. 15, 2021

Related U.S. Application Data

(60) Provisional application No. 62/672,646, filed on May 17, 2018.

(51) Int. Cl.
| | |
|---|---|
| *A61L 27/60* | (2006.01) |
| *A61K 38/17* | (2006.01) |
| *A61L 27/26* | (2006.01) |
| *A61L 27/54* | (2006.01) |

(52) U.S. Cl.
CPC .......... *A61L 27/60* (2013.01); *A61K 38/1709* (2013.01); *A61L 27/26* (2013.01); *A61L 27/54* (2013.01); *A61L 2300/102* (2013.01); *A61L 2300/252* (2013.01); *A61L 2300/404* (2013.01); *A61L 2300/41* (2013.01); *A61L 2400/12* (2013.01)

(58) Field of Classification Search
None
See application file for complete search history.

(56) References Cited

U.S. PATENT DOCUMENTS

| | | |
|---|---|---|
| 2017/0196966 A1 | 7/2017 | Henderson |
| 2017/0319744 A1 | 11/2017 | Raoufi |
| 2018/0043291 A1 | 2/2018 | Baer et al. |

OTHER PUBLICATIONS

Armstrong et al., "Validation of a diabetic wound classification system: the contribution of depth, infection, and ischemia to risk of amputation," Diabetes Care, May 1, 1998, 21(5):855-9.
Bello et al., "Tissue-engineered skin," American Journal of Clinical Dermatology, Oct. 2001, 2(5):305-13.
Boateng et al., "Wound healing dressings and drag delivery systems: a review," Journal of Pharmaceutical Sciences, Aug. 1, 2008, 97(8):2892-923.
Dreifke et al., "Current wound healing procedures and potential care." Materials Science and Engineering: C, March 1, 2015, 48:651-62.
Frykberg et al., "Challenges in the treatment of chronic wounds," Advances in Wound Care, Sep. 1, 2015, 4(9):560-82.
Gurtner et al., "Wound repair and regeneration," Nature, May 2008, 453(7193):314-21.
Jayakumar et al., "Biomaterials based on chitin and chitosan in wound dressing applications," Biotechnology Advances, May 1, 2011, 29(3):322-37.
Ma et al., "Collagen/chitosan porous scaffolds with improved biostability for skin tissue engineering," Biomaterials, Nov. 1, 2003. 24(26):4833-41.
Mahmoudi et al., "Multiscale technologies for treatment of ischemic cardiomyopathy," Nature Nanotechnology, Sep. 2017, 12(9):845-55.
Ovington, "Advances in wound dressings," Clinics in Dermatology. Jan. 1, 2007, 25(1):33-8.
PCT International Preliminary Report on Patentability in International Appln. No. PCT/US19/32683, dated Nov. 17, 2020, 7 pages.
PCT International Search Report and Written Opinion in International Appln. No. PCT/US19/32683, dated Sep. 24, 2019, 16 pages.
Perretti et al. "Lipocortin-1 fragments inhibit neutrophil accumulation and neutrophil-dependent edema in the mouse. A qualitative comparison with an anti-CD11b monoclonal antibody," The Journal of Immunology, Oct. 15, 1993, 151(8):4306-14.
Werdin et al., "Evidence-based management strategies for treatment of chronic wounds," Eplasty, Jun. 2009, vol. 9, 11 pages.
Zhong et al., "Tissue scaffolds for skin wound healing and dermal reconstniction," Wiley Interdisciplinary Reviews: Nanomedicine and Nanobiotechnology, Sep. 2010, 2(5):510-25.

*Primary Examiner* — Hasan S Ahmed
*Assistant Examiner* — Randeep Singh
(74) *Attorney, Agent, or Firm* — Fish & Richardson P.C.

(57) ABSTRACT

In some embodiments, a method of fabricating a skin wound patch includes preparing a biopolymeric solution comprising chitosan, collagen, chondroitin sulfate, elastin, hyaluronic acid, follistatin-like 1 (FSTL-1), iron oxide nanoparticles, and AC2-26 peptide, filtering the biopolymeric solutions through a filter membrane, extruding the biopolymeric solution through an extrusion device to form a nanofibrous composite, collecting the extruded nanofibrous composite on a sterilized plate, and drying the extruded nanofibrous composite into a solid patch. In some embodiments, a skin wound patch includes homogeneously distributed biomolecules, skin materials, pro-inflammatory, and antibacterial agents. In further embodiments, a method of treating a chronic skin wound in a subject in need thereof can include applying any of the patches described herein.

19 Claims, 10 Drawing Sheets

NANOFIBROUS SCAFFOLDS TO HEAL CHRONIC SKIN WOUNDS

CLAIM OF PRIORITY

This application is a national stage application under 35 USC § 371 of International Application No. PCT/US2019/032683, filed on May 16, 2019, which claims the benefit of U.S. Provisional Application Ser. No. 62/672,646, filed on May 17, 2018. The entire contents of the foregoing are incorporated herein by reference.

TECHNICAL FIELD

This invention relates to scaffolds for healing chronic skin wounds.

BACKGROUND

A chronic wound is a wound that fails to heal and produce anatomic and functional integrity over a period of 3 months. A common chronic wound is a diabetic wound, a devastating and costly complication of diabetes that can increase the risk of amputation.

SUMMARY

This disclosure describes a method (with scale-up capacity) for fabrication of a porous engineered nanofibrous scaffold with interconnected nano- and macro-pores with proper nutrient and exudates transfer, cell filtration, attachment, growth, signal induction, and proliferation, by using a nano-extrusion approach. Various types of healing-promoting biomolecules, including vascular endothelial growth factor (VEGF) and follistatin-like 1 (FST-1), together with an antibacterial agent (superparamagnetic iron oxide nanoparticles) are incorporated in the nanofibrous structure of the scaffold during the extrusion process. Both animal and human studies reveal the unique bacterial-free healing role of the developed scaffolds in a wide range of chronic skin wounds (e.g., diabetes, burn, injuries, and bedsores).

Regarding the essential component of human skin, the nano-extrusion of specified biopolymers and therapeutic cocktails/biomolecules without excess manipulations preserves intrinsic characteristics of the biopolymers, prompting cell responses to the scaffolds. The length of the interwoven nanofibers of these applied viscoelastic polymers can reach to a micrometer, providing acceptable mechanical strength. Due to adhesion strength provided by the strong mechanical properties of nanofibrous structure and hydrophilic nature of applied biopolymers, the scaffold can attach to any anatomic site without the need for secondary coverage. With ease of handling, these scaffolds fabricated with simple, scalable and cost-effective methods could be used in a variety of applications.

In some embodiments, a method of fabricating a skin wound patch includes preparing a biopolymeric solution comprising chitosan, collagen, chondroitin sulfate, elastin, hyaluronic acid, follistatin-like 1 (FSTL-1), iron oxide nanoparticles, and AC2-26 peptide, filtering the biopolymeric solutions through a filter membrane, extruding the biopolymeric solution through an extrusion device to form a nanofibrous composite, collecting the extruded nanofibrous composite on a sterilized plate, and drying the extruded nanofibrous composite into a solid patch.

The method can include one or all of the following features. The extrusion device comprises a nanoporous membrane. The nanoporous membrane has a pore size between 10 nm to 2000 nm. Feeding the biopolymeric solution through the nanoporous membrane at a constant flow rate. The constant flow rate is between 1-1000 μl/min for a 400 nm pore size membrane. Drying the extruded nanofibrous composite occurs at temperature between 5° C. and 50° C. or at room temperature. Drying the extruded nanofibrous composite occurs at atmospheric pressure or under vacuum. Neutralizing the dried patch with neutralizing agents. The neutralizing agent is sodium hydroxide. Sealing the extrusion device with an O-ring.

In some embodiments, a patch for use in healing chronic skin wounds includes a scaffold having nanofibers, FSTL-1 embedded in the nanofibers, AC2-26 peptide embedded in the nanofibers, and superparamagnetic iron oxide nanoparticles that are physically attached to the scaffold. Features can include that FSTL-1 or AC2-26 peptide is homogeneously embedded in the nanofibers. The nanofibers are 250-450 nm in diameter. The patch has a maximum stress of about 122.5 kPa at an elongation of about 40%, an adhesive strength of about 70.6 kPa and elastic modulus of about 585.3 kPa.

In some embodiments, a skin wound patch includes homogeneously distributed biomolecules, skin materials, pro-inflammatory, and antibacterial agents. In further embodiments, a method of treating a chronic skin wound in a subject in need thereof can include applying any of the patches described herein.

The devices and methods described herein provide several advantages. The patch mimics physico-mechanical properties of skin, has a homogenous distribution of therapeutic biomolecules, accelerates angiogenesis process and proliferation of immigrated cells, has antibacterial properties, and has capacity to resolve prolonged inflammation. The advantages address major chronic wound issues of lack of space for cell recruitment, poor angiogenesis, bacterial infection, and unbalanced inflammation, Additional advantages include low cost due to the simplicity of the manufacturing process and high potential for automation, rapid and high healing efficacy of wound healing, being self-adhesive and eliminating the need for potentiality allergenic skin adhesives, absorbability, lack of need for replacement, and transparency to allow monitoring of healing.

These advantages are realized due to several features. These include homogeneous incorporation of healing biomolecules, essential skin materials, and antibacterial agents in the patch structure, the use of FSTL-1 in the fibrous structure of the scaffolds (which affects angiogenesis and skin repair), use of superparamagnetic iron oxide nanoparticles which provides bacteria-free skin scaffolds both by their intrinsic antibacterial properties and immune activation efficacies, and specific physicochemical and mechanical properties of the scaffolds.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
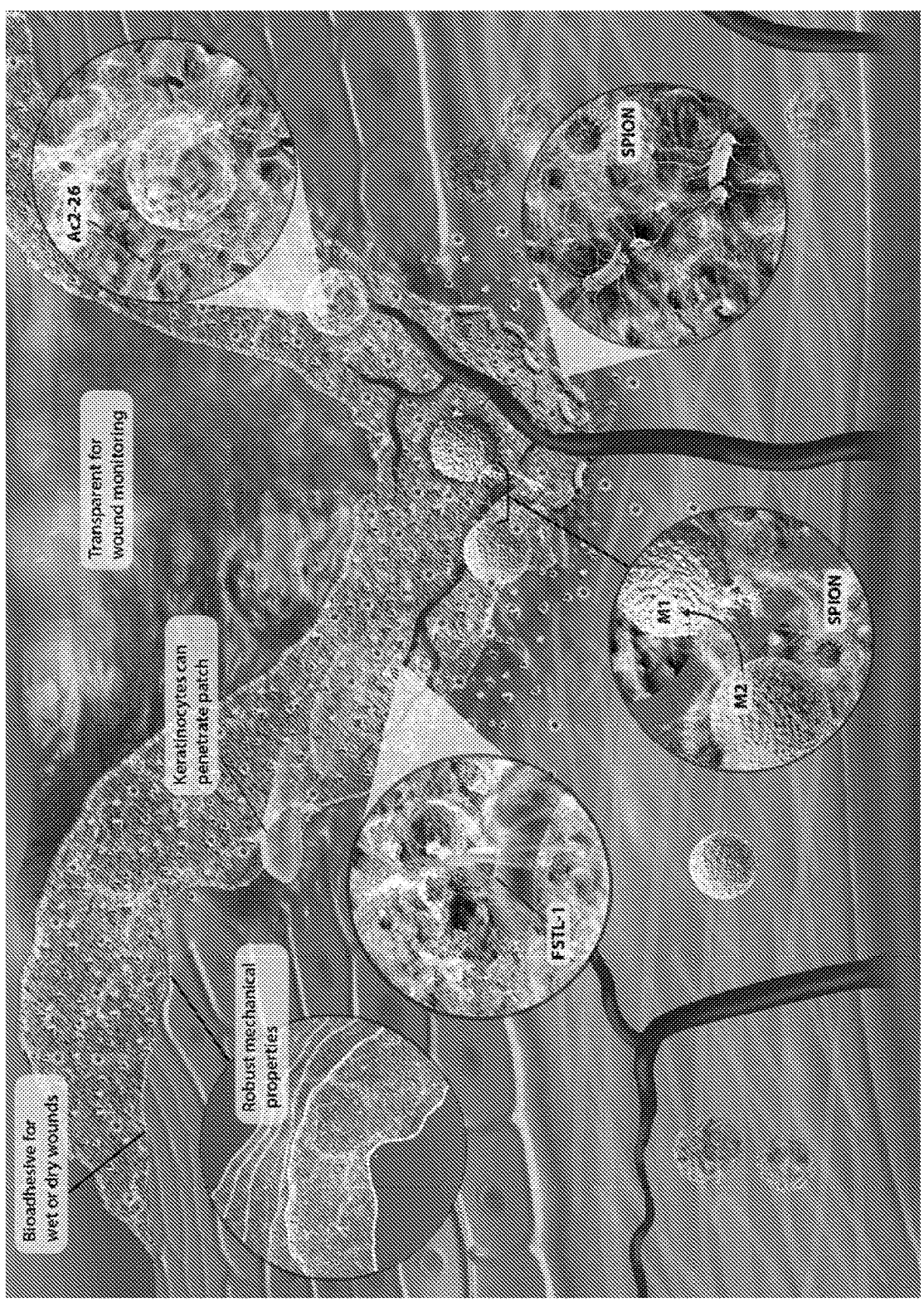
FIG. 1 shows a schematic illustrating the various features of a fabricated skin patch 125.

Numerous marketed products have been developed to minimize the healing duration of diabetic and other chronic wounds. Although these products have positive effects on the wound healing process, their associated limitations (e.g., low-flexibility, inadequate mechanical properties, weak adhesiveness, extensibility, and elasticity) require application of a secondary dressing, which in turn increases the risk of infection or tendency to excess trauma, all of which decrease the required healing outcomes. For example, one gel entraps water and removes exudates (especially in necrotic wounds) and rehydrates tissue, but requires secondary coverage due to its mechanical weakness. A marketed wound dressing hydrogel is not labeled for accelerating wound healing and cure, and is used with a secondary film or hydrocolloid dressing. An allogenic cell-containing skin substitute for diabetic foot ulcer (DFU) healing needs secondary foam dressing. Another requires surgery to remove a silicon layer from the wound surface, causing further trauma as new epithelialized skin may increase the infection risk at the wound site. Moreover, several products have been discontinued due to their weak therapeutic efficacies, high health care costs, delayed or extensive healing, and their complicated preparation methods.

The above examples demonstrate an urgent need for flexible bacteria resistant scaffolds with an effective wound healing capacity. Such scaffolds ideally should include essential components of human skin (e.g., collagen and elastin), mimic skin's extracellular matrix (ECM), present suitable elasticity/stiffness to tolerate moderate forces during normal functions, provide high adhesiveness to attach to the wound surface, and be easy to scale-up.

General Description and Overview of Patch Characteristics

This disclosure describes a simple method (with scale-up capacity) for fabrication of a porous engineered nanofibrous scaffold with interconnected nano- and macro-pores with proper nutrient and exudates transfer, cell filtration, attachment, growth, signal induction and proliferation, by using a nano-extrusion approach. Healing biomolecules, including VEGF and FSTL-1, together with antibacterial superparamagnetic iron oxide nanoparticles are incorporated in the nanofibrous structure of the scaffold during the extrusion process.

The multifunctional nanofibrous composite patch efficiently addresses the main challenges associated with healing of chronic wounds including i) providing a suitable environment in which cells can easily proliferate, rapidly multiply and form new blood vessels, ii) preventing and reducing existing bacterial infection and iii) minimizing unbalanced and prolonged inflammation. The patch contains multi-functional biomolecules (e.g., pro-angiogenics such as FSTL-1, and anti-inflammatories such as Ac2-26) within its fibrous framework to accelerate angiogenesis and cell proliferation while minimizing the risk of bacterial infection and prolonged inflammation in chronic wounds. Investigations have revealed accelerated regeneration with no sign of scar formation, immunological reaction, or cytotoxicity.

Biopolymers (e.g., collagen, chondroitin sulfate, and elastin) were selected to enable the patches to mimic the required physicochemical and mechanical characteristics of human skin including flexibility, stiffness, and adhesiveness. Low molecular weight hyaluronic acid was used to help induce fibroblast differentiation and collagen type I expression which in turn can improve the wound healing and minimize scar formation. Chitosan was employed in the patch due to its high moist absorptive capacity, bio-adhesiveness, and bacteriostatic properties.

The biopolymers' structure remains intact after the extrusion process, which was confirmed by FTIR spectroscopy analysis. The patch provides a unique capacity for water retention, proper nutrient and exudate transport, cell filtration, attachment, growth, signal induction and proliferation that mimics the skin milieu. In addition, the nano-extrusion of the employed biopolymers preserves the essential physico-mechanical properties of human skin and the retained intrinsic characteristics of the biopolymers while promoting cellular responses to the patches. Nanoextrusion processes using viscoelastic polymers also results in interwoven nanofibers with lengths of several micrometers, which facilitates gaining the desired mechanical strength. The strong mechanical properties of the nanofibrous structure and the moist absorptive and bio-adhesive nature of the applied biopolymer scaffolds yields self-adhesive dressings which allow their attachment to wounds in any anatomic site without using secondary coverage. In preferred embodiments, the nanofibers are about (i.e., +/−10%) 350-450 nm in diameter.

The physico-mechanically stable polymeric scaffold was functionalized by incorporating a pro-angiogenic molecule, e.g., follistatin-like 1 (FSTL-1), and optionally an anti-inflammatory agent such as pro-resolving mediator Ac2-26 peptides, linked to the fiber structures during the nanoextrusion process to enhance angiogenesis and the anti-inflammatory capability of the patch to prevent and cure prolonged inflammation. FSTL-1 was homogenously incorporated in the wound healing patch (through nano-extrusion) to induce angiogenesis and to promote cell proliferation. Another benefit of incorporating FSTL-1 in the wound healing patch is its capacity to bind to activins proteins to antagonize their dark effects (e.g., skin tumorigenesis and scar formation) during the wound healing process. Exemplary sequences of human FSTL-1 are provided in GenBank at Acc Nos. NM_007085.5 (mRNA) and NP_009016.1 (protein); FSTL-1 can be produced recombinantly or purified from natural sources using methods known in the art.

In addition to FSTL-1, anti-inflammatory agents can also be included, e.g., pro-resolving peptides Ac2-26 can be included. Ac2-26 is a small and stable peptide known as an effective inflammation resolving agent in several disease models. The critical role of pro-resolving mediator Ac2-26 peptides in tempering prolonged inflammation, mainly in atherosclerosis plaques has been reported by various research groups. Ac2-26 is a small fragment of annexin A1 comprising the sequence (N-acetyl-AMVSEFLKQAWFI-ENEEQEYVQTVK (SEQ ID NO:1); see, e.g., Perretti et al., J Immunol 1993; 151:4306-4314.

In preferred embodiments, the novel wound dressing patch introduced here is based on chitosan, which has antimicrobial properties due to the presence of charged groups in the polymer backbone and their ionic interactions with bacteria wall constituent. TNF-α, IL1, IL6, MCP-1, and CD40L are also possible.

To further enhance the antimicrobial properties of the patches, FDA-approved superparamagnetic iron oxide nanoparticles (SPIONs), e.g., ferumoxytol, conventionally used for treatment of iron deficiency anemia in adult patients, are used to aid to resolve the infection complications of chronic wounds. Recent studies have revealed that SPIONs have two unique functions: i) intrinsic antibacterial effect resulting in reduction of bacterial infection, and ii) changing the functionality of macrophages from M2 to M1. Here, macrophage activation may help intrinsic antibacterial properties of the SPION ferumoxytol to remove the bacterial infection associated with chronic wounds. The cellular uptake of ferumoxytol can be increased by the formation of a protein corona on the surface of the SPIONs (e.g., a layer of proteins surrounding the nanoparticles after their interactions with biological fluids). As the functionalized patches interact with the extracellular portion of the wound tissue, the SPION ferumoxytol will be covered by a corona of proteins and enhance their interactions with macrophages which, in turn, will facilitate removal of bacterial infection in combined with ionic interactions of chitosan groups with functional group of the cell wall of bacteria.

FIG. 1 shows a schematic illustrating the various features of an exemplary fabricated skin patch 125. These include its unique structure and composition (including carefully selected biopolymers) that provide the essential microenvironment for efficient wound healing and ease of clinical use, including easy application and self-attachment to the wound site without the use of adhesives through its robust mechanical properties, and enabling cell migration. In addition, the nanofibrils of the patch contain FSTL-1 to accelerate angiogenesis and cell proliferation, SPIONs to coax macrophages from an M2 to M1 phenotype and remove pathogenic bacterial colonies, and Ac2-26 to tamp down any prolonged inflammation.

Fabrication of the Patches

Figure 2:
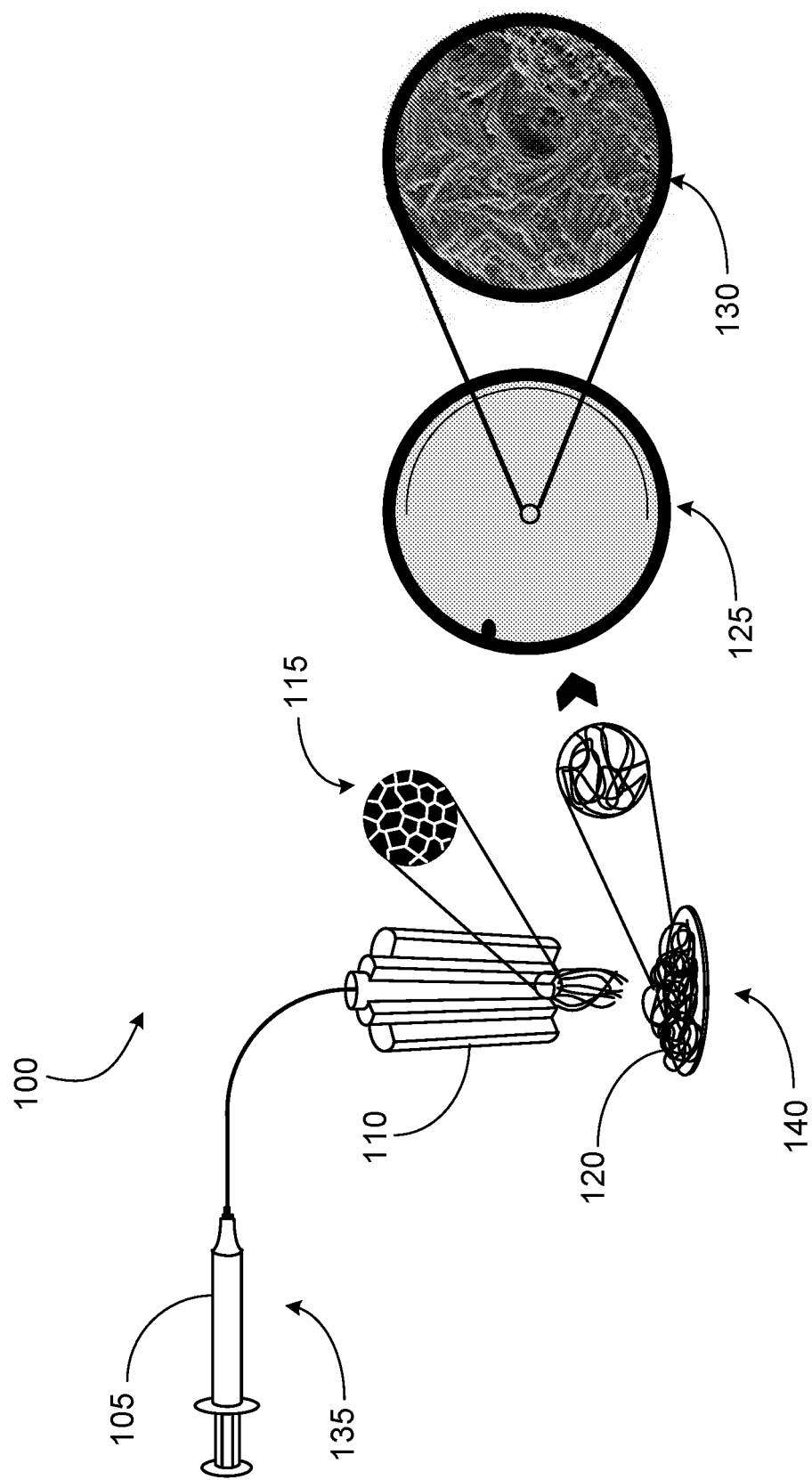
FIG. 2 is a schematic sketch of custom-designed extrusion setup for lab scale production of wound skin patches.
Figure 3A:
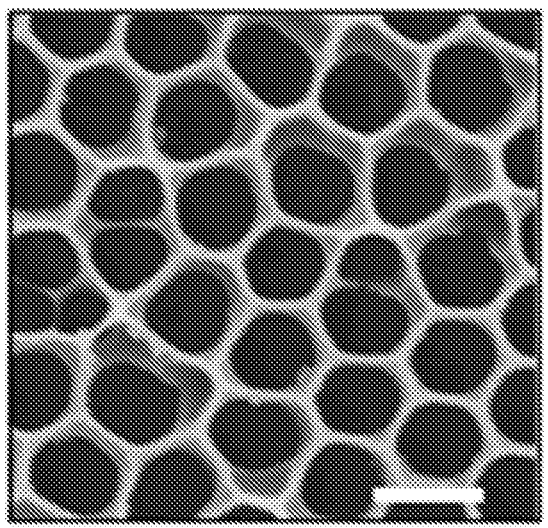
FIGS. 3A-D show various microscopy images of the skin patches.
Figure 3B:
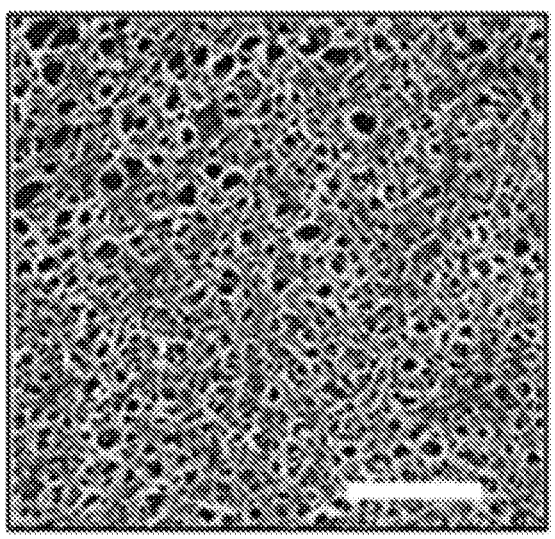
Figure 3C:
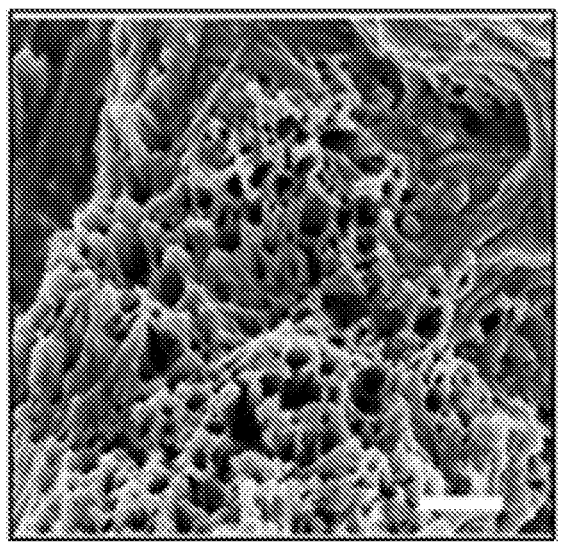
Figure 3D:
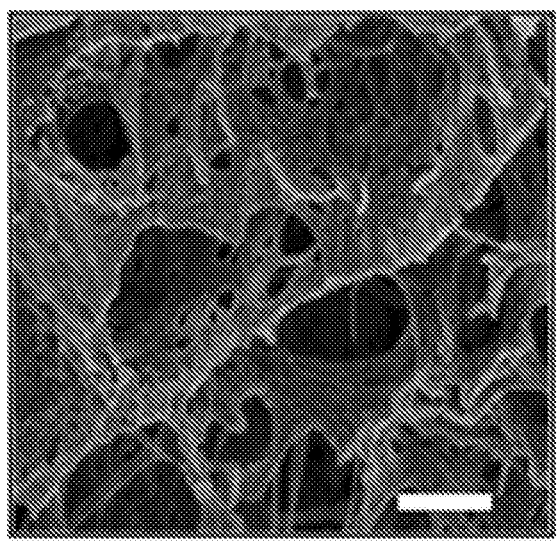

FIG. 2 shows a schematic sketch of a custom-designed setup 100 for nano-extrusion of engineered nanofibrous patches with interconnected nano- and macro-pores. As shown, a biopolymeric solution 105 is prepared and then extruded through an extrusion device 110 including a nanoporous membrane 115 to form a nanofibrous solution 120. That solution is then turned into the skin patch 125, based on a nanofibrous-porous scaffold 130.

In detail, a biopolymeric solution 105 is prepared at specified concentrations. Different combinations prepared in different buffer solutions are presented in Table 1. The mixed composite solutions were filtered through a 0.22 µm filter membrane to remove undissolved fragments. The nanoporous membrane 115 (with optimized pore size of ceramic membrane of 400 nm) is mounted in the extrusion device 110 and sealed with an O-ring. Different membrane pore sizes were used in trials (e.g., 100-800 nm) and 400 nm size selected to achieve the required skin properties of the patch.

The extrusion process was conducted under controlled temperature (selected so that the biopolymer remains intact) to facilitate evaporation of the solvents of the extruded nanofiber. The biopolymeric solution 105 was fed to the extrusion device 110 and passed through the biopolymeric membrane 115 by a syringe pump 135 at a constant flow rate. The flow rate can have a wide range depending on the size of membranes and the ultimate required physico-chemico-mechanical properties of the final fibers and the patch. For example, the flow rate can be 200 µl/min. The constant flow rate can range between 1-1000 µl/min for a 400 nm pore membrane. Other flow rates (1-1,000,000 µl/min) can also be used for membranes with higher pore sizes. Parallel membranes can also be used, particularly when scaling up.

The resulting extruded nanofibers 120 are collected on sterilized plates 140 of different sizes required for different wound areas. All extrusion and drying processes are performed under clean room (class D) conditions. In one example, the extruded nanofibrous composites 120 are dried at room temperature in a culture hood overnight. As the components and the concentration of each element of the patch can significantly change based on the wound type for which the final patch is destined, the drying temperature can range from 5 to 50° C., under atmospheric pressure, or low pressure (e.g., vacuum) conditions. In general, the drying of the extruded nanofibers occurs at temperature range that keeps the functionality of all the components of the extruded nanofibers intact.

After drying, the patches are neutralized by sodium hydroxide. The pH of the patches is measured before and after neutralization, and the processed patches were stored at the refrigerator.

TABLE 1

| Protein/Polymer | Buffer | Concentration (mg/ml) | Portion (%) |
| --- | --- | --- | --- |
| Chitosan | Acetic Acid (1%)/PBS | 3.5 | 80 |
| Collagen | PBS | 0.3 | 5 |
| Chondroitin Sulfate | PBS | 0.5 | 5 |
| Elastin | PBS | 0.3 | 5 |
| Hyaluronic Acid | PBS | 0.5 | 5 |

In some embodiments, marine source derived pharmaceutical grade chitosan (MW 100-250 kD) suitable for oral and systemic administration can be used. A solution of bovine type I atelocollagen solution suitable for medical device manufacture, as well as GMP cell culture and wound dressing manufacture can be used.

Bovine neck ligament elastin can be solubilized with a hot oxalic acid solution, clarified, dialyzed and lyophilized. The preparation is a salt-free, water-soluble powder that readily forms a coacervate at PH 5.0 and 37° C. Chondroitin can be sulfite derived from porcine cartilage. AQUACEL Extra® (ConvcaTec, USA), AQUACEL Ag (ConvaTec, USA) can be applied as a standard treatment wound dressing. The incoming materials are tested for bioburden and endotoxin, the solution 105 before extrusion are tested for bioburden and endotoxin to ensure the requirements are met. The final product is tested for sterility and endotoxin. Water for injection is used when needed. For the clinical trials described below, a cleanroom class ISO 7 of a pharmaceutical company was used for production of the patches.

The following series of tests were carried out to characterize the scaffolds 130 and resulting patches 125 and their fabrication as described herein. The tests used apply to characterization of the patches themselves, as well as characterization of patches after in vitro and in vivo studies.

FIG. 3 show images of the patches fabricated with biopolymers (polysaccharides and proteins) that were extruded under constant flow rate by the customized setup of FIG. 1. FIG. 3A shows the nano-porous membrane structure through which the polymer solutions are extruded (scale bar, 500 nm). FIG. 3B show a multilayer nanofibrous porous patch (scale bar, 5 µm), FIGS. 3C and 3D show scanning electron microscopy (SEM) and cryo-SEM imaging of patch pore size distribution (scale bars: 500 nm).

To obtain these data, field emission scanning electron microscopy (FESEM) was used to examine the pore size and morphology of scaffolds at 3.0 kV accelerating voltage. The samples were fixed by mutual conductive adhesive tape on aluminum stubs and covered with a 10 nm thickness of a gold film by sputtering. This morphological analysis of the patch revealed the presence of a network of uniform nanofibers with narrow diameters of 106±21.7 nm and length 1.8±0.31 μm.

The pore size distribution was calculated based on the Kelvin equation by Barrett-Joyner-Halenda (BJH) analysis, with a mean pore size of 7.1±0.4 nm. The BET and BJH analyses were used to determine the surface area, porosity percentage, and the pore size distribution by mercury-intrusion porosimetry using pore sizer. The results of the parallel Brunauer-Emmett-Teller (BET) analysis confirmed the similarity of the structure of the patch to type IV isotherm according to IUPC classification, typical of mesoporous, solids, with a total surface area of 22.54±1.63 $m^2/g$.

Morphological analysis by SEM and cryo-SEM imaging of patches showed the existence of microporosity and macroporosity within the patch network. The presence of porosity within the framework of the polymeric patches provides an ideal environment for efficient function of extracellular matrix (ECM) and its interaction with cell surface and other cellular components. ECM plays a critical role in the healing process of chronic wounds; for example, the bidirectional interaction between growth factors and variety of ECM proteins will increase cell proliferation in general and it contributes to the development and generation of epithelial leading to fast healing of chronic wounds.

The physico-chemical characteristics of the patches were further analyzed by Fourier-transform infrared (FTIR) spectroscopy, differential scanning calorimetry (DSC), and thermogravimetric analysis (TGA). For chemical characterization, infrared spectra of scaffolds were collected on an FTIR spectrometer, KBr pellets were prepared and scanned over a range of 400-4000 $cm^{-1}$ (five scans at a resolution of 10 $cm^{-1}$). FTIR revealed that the chitosan concentration in the patches influences the specific FTIR bands of collagen and hyaluronic acid. As the chitosan concentration in the patches increases, a decrease in the amide I and III bands intensity is observed.

The thermal stability of the scaffolds was measured by DSC and TGA analyzers and underwent a heating procedure from 40 to 400° C. and 0 to 700° C. respectively at a scanning rate of 10° C./min in a nitrogen atmosphere. After calibration with indium and lead standards about 3-5 mg of the scaffolds were weighed and placed into an aluminum pan (an empty aluminum pan was used as a reference for DSC analyzing).

The biological composition of human skin such as live cells, hair follicles, sweat glands, and sebaceous glands can change the mechanical properties of all skin layers. Therefore, skin composition continuously varies and makes patch engineering more difficult. The elastic modulus reported varies depending on the evaluation methods and test conditions. The evaluation of the rheological behavior of patches can provide valuable insight into the patches cohesive response under mechanical stress.

To analyze the strain-dependent elastic behavior and stiffness of the designed patches used as a substitute for skin, dynamic oscillatory tests were performed by measuring the stored (G', elastic modulus) and lost energy (G", viscous modulus) during a strain cycle. The amplitude sweep tests were performed at variable amplitudes at a constant frequency (10 rad/s). The results of the amplitude strain and stress sweep tests showed that the storage modulus (G'~86 kPa) within the linear viscoelastic (LVE) region was higher than the loss modulus (G"~8.7 kPa). The critical strain ($\gamma_c$) at the end of LVE region was 0.68% and the critical stress of patches was 115 kPa. The amplitude sweep test also revealed the viscoelastic behavior of patches. The intersection of the curves for G' and G" took place at the same deformation point of approximately 10% shear strain. Amplitude sweeps with a shear strain in the range of 0.1-100% at a constant frequency of 10 rad/s, and frequency sweep test with different angular frequencies in the range of 0.1-100 rad/s at a constant strain (10%) in controlled temperature at 37° C. were also performed. To avoid dehydration of hydrated scaffolds, an evaporation blocker system was used during the tests.

Based on the results of the amplitude sweep test for determining the LVE region, a constant strain (0.1%) less than the critical strain ($\gamma_c$) was applied for frequency sweep tests. The obtained results showed that over the whole ranges of frequency, the storage modulus (G'~10-30 kPa) of the patches was significantly higher than the loss modulus (G"~1-3 kPa), G'>G" in the whole frequency range analyzed revealed that the elastic behavior prevailed over the viscous one for the present patches, which points to their viscoelastic solid-like behavior with a strong structure and stiffness, hence, with a suitable mechanical strength for the intended application. The overall rheology of the patches represents a non-linear elastic behavior similar to human skin mechanical properties.

Figure 4:
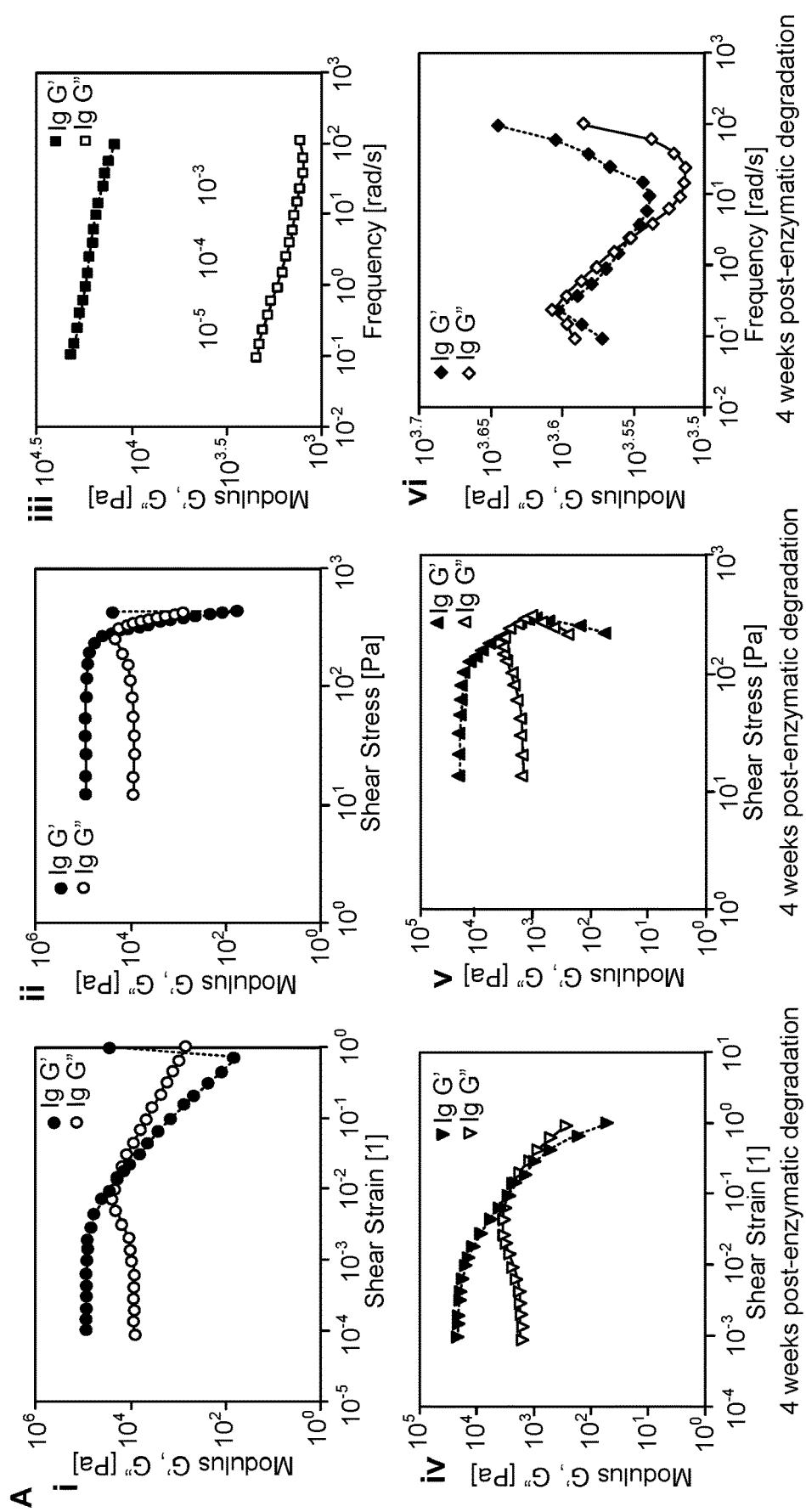
FIG. 4 shows exemplary results of testing mechanical properties and stability of the patch after 28 days of enzymatic degradation in vitro.

FIG. 4 shows exemplary results of evaluating the mechanical properties and stability of the patch after 28 days of enzymatic degradation, by dynamic oscillatory tests, an important point for their successful long-term healing capability provided that enzymes such as collagenase are present in relatively high concentration in chronic wound sites. Shown is the rheological behavior of a highly hydrated patch evaluated by dynamic oscillatory tests with (i) an oscillatory amplitude strain sweep, (ii) oscillatory amplitude stress sweep, (iii) oscillatory frequency sweep of patch. Following in vitro enzymatic degradation by lysozyme/collagenase enzymatic degradation shows changes in (iv) the oscillatory amplitude strain sweep, (v) oscillatory amplitude stress sweep, and (vi) oscillatory frequency patches after 28 days of incubation.

A certain weakening of the patches' structure and, thus, a softer mechanical strength was observed after incubation compared to the non-degraded patch, but being still suitable to support wound healing. In this regard, the storage (~18 kPa) and loss (~1.86 kPa) moduli of the patches after degradation maintained their nonlinear behavior with G'>G", indicating the preservation of their viscoelastic microstructures even after enzymatic degradation. Frequency sweep tests also demonstrated that the patches behavior largely maintained their microstructure, that is, their elastic solid-like behavior after 28 days of degradation with G' and G" values of ~9.8 kPa and ~3.4 kPa, respectively. Thus, rheological properties correlation and mechanical properties measured with different methods proved that the patches have sufficient mechanical stiffness to support the stretch of biological tissues during normal functioning.

The elastic modulus was also calculated by micro-rheology. The force-indentation of atomic force microscopy (AFM) of the patch from dried to the hydrated state increased since the elastic modulus and elongation are directly influenced by the presence of plasticizers such as water. Representative force-separation plots (on approaching and retracting from the patch surfaces) on dry and hydrated patches and their stiffness were calculated from force-indentation curves. Young's modulus of patches also decreased after patch hydration (3400 vs. 526 kPa for dry and hydrated patches, respectively) which denotes the weakening of its structure upon water induced-swelling.

The obtained dried patches were also tested to determine the maximum applicable stress before breaking through the application of a tensile force. The maximum stress at the breaking point of the patches was 122.5 kPa. Additionally, the elongation of the patch at the breaking point ($E_b$ %), which is the increase (in %) in patches length until breakup, was determined to be approximately 42%. The elastic modulus was calculated as the slope of the force/displacement (stress/strain) curve at the linear region, with values of 3.69 MPa for the patches for the hydrated patches these quantities were 69.7 kPa, 24.6% and 1.53 MPa, respectively. Scaffold structure alteration in response to mechanical stimuli was evaluated according to the standard test method for tensile properties of thin films (ASTM D882-12, Protocol D882 covers films and sheets less than 1 mm thickness) with a strain rate of 1 mm/min using a texture analyzer.

The AFM measurements were conducted under normal ambient conditions in contact mode. The data were processed for the determination of root mean square roughness (RMS) and peak to valley (Rpv) roughness. Force spectroscopy (FS) measurements were performed using scanning probe equipment and built-in software. In the force-versus-displacement curves (F-δ, also known as force curves) the AFM probe bends downwards due to van der Waals and water meniscus interactions in a process known as jump to contact when probe moves towards the sample. Similarly, jump off contact occurs during the unloading process, which is related to the adhesion forces between the tip and sample surface during contact. F-δ curves were acquired from AFM controller and built in software by applying vertical force around nN range. The resulting data is a force curve that allows assessing elastic and plastic properties of the samples. The slope of force curve describes the elastic properties of a sample. The value of Young's Modulus were calculated using the Hertziant model. To evaluate microrheology of live tissues, Young's modulus and stiffness mechanical properties of the scaffolds were calculated by nano-indentation (Hertz model, the slope of the line drawn between 0 nN and 80 nN).

Following the guidelines from the American Society for Testing Materials (ASTM), adhesion tests were performed to determine the adhesiveness to the skin and maintenance at the wound site of patches for a prolonged period of time. The adhesion properties of the scaffolds were evaluated based on the ASTM F2458-05 protocol. For comparison, fresh porcine skin was purchased from Slaughterhouse and utilized because of its similarity to human skin. A 20*10 mm$^2$ portion of porcine skin was fixed between two glass slides by glue with an interspace of 8 mm. The skin was separated at the middle point to induce a wound and the adhesiveness was determined by loading a force of 1 mm/min to detach scaffolds from the surface of the incised porcine skin. The adhesive strength, Eb % and elastic modulus of patch were determined to be 70.6 kPa, 23.2%, and 585.3 kPa, respectively. In the light of these data, designed patches are capable of providing an efficient adhesiveness for their attachment to human skin while maintaining sufficient structural integrity.

To determine the swelling ratio of scaffolds, the specified weight of the scaffold was immersed in phosphate buffered saline (PBS) solution (pH 7.4) and incubated at 37° C. for 8 days. Then the sample was taken out at specific intervals and weighted after removing the surface water of the scaffolds by filter paper. The gel fraction of scaffolds was assessed after 8 days, about 10 mg of completely dried scaffolds was soaked in 20 ml of deionized (DI) water at room temperature and the media was refreshed every 96 hours, and after washing out the soluble portion, the scaffolds were freeze-dried and weighted. Water contact angle test was measured using a goniometer on the basis of the sessile drop method.

Enhanced hydrophilicity improves water retention, polymer swelling, and expansion, paving the way for an efficient nutrient transfer and oxygenation while facilitates drainage and debris removal, decreasing the risk of infection at the wound site and promoting tissue reconstruction. It was observed that at short incubation times (<12 h) the patches displayed a high swelling ratio approximately 3 fold patches net weights (258.4±4.5%, while the opposite trend was found at longer incubation times of up to 1 week, reaching a maximum after 5 days (value of 331.0±12.5%, respectively, p<0.05). The long fiber sizes and porosity of patches would explain such behavior, that is, large fibers swell faster but to lower extents due to saturation.

The hydrophilicity of patches was additionally corroborated by measuring water contact angles, which were approximately 41° confirming that the surface hydrophilic character of patches. Stability tests of patches along 8 days of incubation denote that the most parts of the patch remained intact in aqueous media, with gel fractions above 87.0±3.7%, so the dissolution rate was rather low. This helps in understanding the observed slight decreases in swelling ratios after 5 days of patches incubation, which might be related to the observed polymer degradation and subsequent mass loss of patches. Due to the presence of enzymes such as lysozyme and collagenase in high concentrations at chronic wound sites, also examined was the effect of enzymatic degradation on the scaffolds for 28 days in the presence of both enzymes individually and in combination. The degradation ratio calculated on the basis of the patch weight loss was measured at days 1, 7, 14, 21, and 28. Statistical analysis showed that in the absence of enzymes the patch mass loss was 22.2±3.9% (control groups), which were significantly lower than those in the presence of lysozyme (36.3±4.7%), collagenase (32.4±4.6%), and lysozyme/collagenase (41.1±3.2%) after 28 days of incubation. The control group's degradation profile after 2.8 days did not show any remarkable change due to its constant degradation via erosion and hydrolysis. Conversely, it was observed that the enzymatic degradation was time-dependent, that is, the degradation of patches is progressively more important as a consequence of the hydrolysis of glycoside and amide bonds within the patch structure. In this regard, the main cleavage site for chitosan, the main component of the present patches, is its glycoside bonds, while N-(1-phenylalanine)-4-(1-pyrene) butyramide is the main cleavage site of collagen for lysozyme, and collagenase cleaves all three alpha helical chains of collagen type I.

Scaffold degradation rate was quantified by measuring scaffolds' dry weight loss after incubation in 10 ml of PBS (pH 7.4) containing 0.5 mg lysozyme (58,100 IU), 0.5 mg collagenase type I (≥125 CDU), and 0.5 mg collagenase/0.5 mg lysozyme in PBS at 37° C. until 28 days. The enzymatic solution was refreshed daily, and the scaffolds were weighted after washing, lyophilizing and drying at 1, 7, 14, 21, and 28 days. In vitro enzymatic degradation was measured based on the weight loss. The control group scaffolds were immersed into a solution without enzyme, and the dissolution rate of the scaffolds were evaluated at the above time points as well.

In Vitro Biocompatibility

The fabricated patches were subjected to in vitro biocompatibility tests. The degradation ratio by selected enzymes after 28 days of incubation ascertained that the biodegradation rate of the polymers of the patch is largely enhanced, while the patch degradation rate in the absence of aqueous media is rather low, as also confirmed by the swelling and gel fraction measurements. In addition, the analysis of the mechanical properties of the patches during the 28 days of degradation was assessed by dynamic oscillatory tests, which showed that the hydrogel patches maintain a sufficient mechanical strength, which is a crucial factor for supporting the damaged tissue until complete regeneration.

Based on the ASTM standard cytotoxicity tests for biomedical devices, the in vitro cytocompatibility of the engineered patches was evaluated by the CCK-8 proliferation assay using human keratinocyte HaCaT cells and mouse fibroblast Balb cell lines, which are more sensitive than other cell lines to any toxic materials. Cells were cultured on the surface of the patches as a substrate in 96 well plates and incubated for 1, 3, 7, and 14 days. Two different toxicity tests were performed: in one sets of experiment, the cell were incubated directly on the surface of patches and the induced toxicity was measured after 24 and 72 h; and in the second experiment, the patches were incubated in cell culture medium for 96 h, and the lixiviate fluid used as incubating medium for cells was analyzed for cell induced toxicity at the same periods of time. In any case, the findings depicted that the fabricated and functionalized novel polymeric patches not only are non-toxic but also they are capable of promoting cell attachment, growth and proliferation. Therefore, cell viabilities of patches incubated with Balb and HaCaT cells were 112±1% and 94±7%, and 137±19% and 126±7% after 24 and 72 h of incubation, respectively. Moreover, the induced cytotoxicity of the patches' leachable material in Balb and HaCaT cells was also quantified to be 77±1% and 98±6%, and 89±9% and 113±6% after 24 and 72 hrs, respectively, confirming biocompatible and non-toxic nature of the designed patches. Furthermore, confocal microscopy analysis showed the presence of many viable cells after 72 h on the patch surfaces, corroborating their cytocompatibility.

Monitoring of the cultured cells for 1 and 2 weeks revealed that cell proliferation at the patch surfaces was higher than the control group, and an extended layer of cells was observed to develop. Data are shown as mean±SD. Light microscopy results of cell growth on a patch after 7 and 14 days confirms the viability, adhesion, and proliferation of cells onto the functionalized patches. Moreover, the results showed an elevated cell growth and proliferation, cell infiltration and adhesion.

In addition, the release of pro-inflammatory cytokines such as tumor necrosis factor-α (TNF-α), and interleukin 6 (IL-6), as a factor of potential risky adverse cell response reactions upon patch implantation, were quantified. Enzyme-linked immunosorbent assay (ELISA) assays showed that the production of these pro-inflammatory cytokines remained rather low supporting the non-toxic and non-pro inflammatory nature of the patches. The patch-induced toxicity was further measured by monitoring the presence of reactive oxygen species (ROS), which is an indication of potential toxicity. ROS production level assays were also carried out in both the former cell lines. Negligible values of ROS were detected that were similar to the control group. Moreover, cells were mostly active, attached to the patch surfaces, and able to proliferate. This indicates that the presence of patches did not elevate the ROS concentration to toxic levels as occurred for those of the positive control group, which displayed significant alterations in their morphology state indicative of an apoptotic state.

The HaCaT and Balb/3T3 clone A31 mouse embryonic fibroblast cells were grown at standard culture conditions (5% $CO_2$ at 37° C.) in Dulbecco's modified Eagles medium (DMEM) supplemented with 10% (v/v) FBS, 2 mL-glutamine, 1% penicillin/streptomycin, 1 mM sodium pyruvate, and 0.1 mM non-essential amino acids (NEAA).

According to the ISO 10993-5 standard, two types of cell culture tests (direct contact and elution) were carried out to assess in vitro cytotoxicity of biomedical devices. Keratinocyte HaCaT and fibroblast Balb cells were used to evaluate scaffolds cytotoxicity. Cell suspension of 100 μl containing $10^4$ cells per well were seeded onto scaffolds in 96 well plates and incubated at 37° C. in a humidified atmosphere with 5% $CO_2$. Following the incubation, at the determined time points (1, 3, 7, and 14 days) 10 μL of CCK-8 was added to each well and incubated for 1 hour. Finally, cell viability was quantified at each time point by measuring the absorbance at 450 nm using a microplate reader. To carry out the elution test, 20 mg of scaffolds were incubated for 96 hours at standard cell culture condition to obtain scaffolds leachable materials. Then 100 μl of scaffolds lixiviate were incubated with a cell suspension ($10^4$ cells/100 μl) for 24 and 72 hours, and the media was removed afterwards. Subsequently, 90 μl of DMEM and 10 μl of CCK-8 reagent were added to each well and incubated for one hour. The cell viability was assessed based on the optical density of formazan at 450 nm.

Calcein AM (CAM)-Propidium Iodide (PI) double labeling was employed to prove cellular viability on the scaffolds by confocal microscopy imaging. $5 \times 10^4$ cells were seeded onto each well of chamber slide that contained scaffolds and then were incubated at 37° C. in a humidified atmosphere with 5% $CO_2$ for 24 and 72 hours. After removing media, 100 μl of CAM solution in DMSO mixed with PI in D-PBS was added to 200 μl of 10 5 cell suspension in each chamber slide and subsequently incubated for 15 min at 37° C. in atmosphere with 5% $CO_2$. Scaffolds' cytotoxicity based on the proportion of live (CAM-positive/PI-negative) and dead (CAM-negative/PI-positive) cells was assessed by confocal fluorescence microscopy. Five different areas of scaffolds were imaged at 490 nm excitation, and at 515 and 545 nm emission for CAM and PI respectively.

To detect intracellular ROS production reflected by scaffolds, a Fluorometric ROS kit was utilized. $10^4$ Balb cells in 90 μL media were seeded onto each well of chamber slide that contained sterilized scaffolds. After 24 hours of incubation, the cell medium was removed. Then 1 μL of diluted 500×ROS detection reagent stock solution with 0.5 mL assay buffer (PBS)/mL of cells media based on the manufacturer's protocol was added to every well of the chamber slide (cell suspensions contained $5 \times 10^4$ cells/well), then incubated in atmosphere 5% $CO_2$ at 37° C. for 30 minutes. As a negative control, cells without scaffolds were treated with a reagent, and as a positive control, hydrogen peroxide ($H_2O_2$) was utilized as an exogenous ROS source. Then the scaffolds ROS production based on live cells was assessed by confocal microscopy. Five different area of scaffolds were imaged at $\lambda ex=640$ nm/$\lambda em=675$ nm. Quantitative evaluation of ROS production was assessed by flow cytometry.

ELISA was performed to evaluate the concentration of pro-inflammatory cytokines secreted by HaCaT and Balb cells after 96 hours of incubation with scaffold. Then, the conditioned media was collected, and levels of TNF-α, and IL-6 were measured by ELISA kits (R&D Systems). The concentrations of these proteins were determined according to the manufacturer's instructions.

In Vivo Analysis

Comprehensive in vivo analysis of the wounds revealed that the patches could substantially accelerate both wound closure and regeneration with no sign of scar formation, immunological reaction, or cytotoxicity. The in vivo therapeutic function of the polymeric patches was probed using classical spontaneous healing rat models of non-infected and infected diabetic wounds.

AQUACEL Extra®, a commercially available soft non-woven sodium carboxymethylcellulose fibers wound dressing, was used as a positive control (this dressing were replaced every 7 days). AQUACEL Ag® (ConvaTec, Princeton, N.J., USA), a commercially available product for infected diabetic and other chronic wounds, which is a soft non-woven sodium carboxymethylcellulose fibrous contains 21 µg/cm$^2$ ionic silver. Evaluated was wound closure during one-month post-intervention by the differently designed patches (see Table 2 for details) including nanofibrous, with FSTL-1 and, Ac2-26 functionalized patches on non-infected diabetic rats comparing with AQUACEL Extra® as a positive control and the negative control group without any intervention after wound incision. Infected diabetic wound healing in animal models that were inoculated by *Staphylococcus aureus* was examined by 4 types of intervention, infected control group without any treatment, treatment by AQUACEL Ag®, SPION ferumoxytol patch, and the composite (having FSTL-1, Ac2-26, and SPION ferumoxytol) patch. The outcomes revealed accelerated wound closure capacity of the patches up to 15 days compared to the controls (that is, with no treatment and treatment with AQUACEL Ag®). It is noteworthy that due to the nature of the classical spontaneous healing rat models, all wounds eventually would be healed (over a month).

Macroscopic planimetry assay using digital camera imaging and ImageJ software that all treatments on non-infected-diabetic groups (even control group) showed significant wound closure after 4 weeks. Wound closure of nanofibrous patch, FSTL-1 patch, Ac2-26 patch, AQAUCEL Extra® treated groups and Control group 4 days post-wound induction were approximately 22.6±3.8%, 53.9±13.3%, 43.47±14.4%, 29.9±11.6%, respectively.

Wound contraction a week post-wound induction demonstrated the higher healing rate of treatment groups by Ac2-26 patch, FSTL-1 patch and nanofibrous patch compared with AQUACEL Extra® and control group (57.3±12.5%, 64.7±9.9%, 85.0±0.4%, 52.4±14.5%, 67.4±1.6%, respectively). Wound closure of AQUACEL, Extra® after 2 weeks of wound induction was significantly lower than other groups including control (56.7±1.6%, P<0.001). Complete wound closure after 4 weeks of all experimental groups was observed, and there was no significant difference among all groups after 28 days of wound incision.

As stated earlier, one of the main complications of chronic wounds is the occurrence of infection. Some clinical and animal studies have demonstrated that the AQUACEL Ag® is an effective and safe dressing for broad range of infected wounds in particular wounds effected by gram-positive bacteria compared with other commercially available silver-based wound dressing materials. The main concern about silver-based antibacterial dressing is the toxic effect of silver on fibroblast cells during the healing process which could prolong the healing process.

Wound closure after 4 days for infected-diabetic rats without any treatment was ~18.6±3.9%. Antibacterial effect of AQUACEL Ag® improved healing up to 35.3±22.3% of contraction. Wound contraction by the Composite and SPION ferumoxytol patches was ~43.0±9.1% and ~64.4±9.2% (respectively) which were significantly higher than AQUACEL Ag® and infected-control groups. One-week post wound induction, the wound closure of the SPION ferumoxytol patch (62.6±27.7%), Composite patch (76.5±12.3%) and control infected (50±24.2%) was significantly higher than AQUACEL Ag® (37.8±8.6%, P<0.01).

TABLE 2

| Patch | Composition | Remarks |
|---|---|---|
| Nanofibrous patch | Extruded nanofibrous patch composed of chitosan, collagen, chondroitin sulfate, elastin, and hyaluronic acid | Providing a suitable environment in which cells can easily proliferate, rapidly multiply and form new blood vessels |
| FSTL-1 patch | Extruded nanofibrous patch composed of chitosan, collagen, chondroitin sulfate, elastin, hyaluronic acid, and follistatin like-1 | Providing a suitable environment in which cells can easily proliferate, rapidly multiply and form new blood vessels; accelerating angiogenesis process |
| AC2-26 patch | Extruded nanofibrous patch composed of chitosan, collagen, chondroitin sulfate, elastin, hyaluronic acid, arid pro-resolving AC2-26 peptide | Providing a suitable environment in which cells can easily proliferate, rapidly multiply and form new blood vessels; minimizing unbalanced and prolonged inflammation |
| SPION patch | Incubated superparamagnetic iron oxide nanoparticles with the extruded nanofibrous patch composed of chitosan, collagen, chondroitin sulfate, elastin, and hyaluronic acid | Providing a suitable environment in which cells can easily proliferate, rapidly multiply and form new blood vessels; preventing and reducing existing bacterial infection |
| Composite patch | Incubated superparamagnetic iron oxide nanoparticles with the extruded nanofibrous patch composed of chitosan, collagen, chondroitin sulfate, elastin, hyaluronic acid, follistatin like-1, and pro-resolving AC2-26 peptide | Providing a suitable environment in which cells can easily proliferate, rapidly multiply and form new blood vessels; preventing and reducing existing bacterial infection; minimizing unbalanced and prolonged inflammation; and accelerating angiogenesis process |

After 2 weeks, wounds contracted in the control group about (39.5±19.3%), which was delayed due to the presence of infection. However, the wound was contracted by AQUACEL Ag® (86.5±6.2%), Composite (97.7±2.5%) and SPION patches (92.9±6.1%). Statistical analysis showed no significant differences between both patch treatment groups and AQUACEL Ag® treatment group healing efficacies after 15 days.

To study the mechanism of healing and progress of wound regeneration for each group, a stereology evaluation with a gold standard method of tissue component assessment was performed with Hematoxylin and Eosin (H&E). To detect collagen bundle formation, Masson's trichrome staining was carried out for all experimental groups at various time intervals. The blood glucose level and weight changes in all rats during the wound healing process were carefully monitored.

Statistical analysis of the stereological assay of the histological study demonstrated that the healing efficacy of nanofibrous, FSTL-1, and Ac2-26 patches was higher compared to that of the AQUACEL Extra® and control groups. The volume of newly formed epidermis at the wound site of the Ac2-26 patch was also higher than that of the nanofibrous patch, FSTL-1 patch, AQUACEL Extra®, and control groups at 4, 7, 15, and 28 days post wound incision. Briefly, the newly formed epidermis of Ac2-26 patch was 33% and 23% thicker than control and AQUACEL Extra® treatment groups after one and 4 weeks of treatment, respectively. As the healing rate of Ac2-26 patch revealed remarkably increase in cellular recovery after one week indicating the critical role of pro-resolving inflammation in the wound healing process. In addition, analysis of the volume density of dermis for the patches showed that the pro-inflammatory Ac2-26 could efficiently affect the wound healing process at 7, 15, and 28 days post-wound induction ($P<0.001$). Stereology analysis of collagen bundle deposition volume density at the wound site demonstrated that at one-week post-wound induction, collagen formation in the wound covered by Ac2-26 patch was significantly higher than other groups ($P<0.001$). After 28 days, collagen deposition (30%) in the wound masked by the nanofibrous patch and Ac2-26 patch was relatively higher than for the other type of patches in all treatment groups.

No sign of prolonged inflammation as a trigger of non-healing wounds was observed as confirmed by the numerical density of neutrophil cells assessment in the nanofibrous, Ac2-26, and FSTL-1 patches treatment groups for 28 days. Statistical analysis of the variance (ANOVA) of the inflammatory cell count after 1 and 4 weeks showed that there was no significant difference between nanofibrous patch, Ac2-26 patch, and FSTL-1 patch, while AQUACEL Extra® group showed higher neutrophil density than the other groups after one week.

The numerical density of fibroblasts, which play a crucial role in the skin structure and function as well as in accelerating the healing rate, was significantly higher in wounds treated with Ac2-26 and FSTL-1 patches compared to those treated with the nanofibrous, AQUACEL Extra® and control patches. Numerical density of fibroblasts in the wound treated with AQUACEL Extra® were extremely lower in the first week of wound healing but reached a maximum level after 28 days. Numerical density of basal cells, which are the main players for wound epithelialization and wound healing processes, were also investigated by the stereology method assay. The results revealed that the density of the basal cells in the Ac2-26 patch treatment group was significantly higher than other groups.

Comparative in-vivo experiments were conducted to evaluate the effect of SPION ferumoxytol containing patches and composite patches on infected wounds compared to the commercially available AQUACEL Ag® patch and control (without any dressing) using a rat model. Analysis of the volume density of newly formed epidermis and dermis (with respect to collagen deposition, neutrophils, fibroblasts and basal cells revealed the unique function of the composite patch to promote a safe and efficient healing process compared to the other groups. Owing to its distinct multifunctional composition including SPION, FSTL1, and AC2-26, the composite patch is capable of removing bacterial, promoting angiogenesis, and minimizing prolonged inflammation.

To investigate the usefulness of patches in the formation of new vessels during the wound healing process, von Willebrand factor (vWF) staining was used to detect new capillary vessels for both non-infected and infected diabetic wounds at 7 and 15 days after wound induction. The outcomes revealed that the FSTL-1 patches could induce capillary vessel formation at the wound site significantly higher than other patches. More specifically, the numerical density of the formed capillary vessels 2 weeks after applying the FSTL-1 patch (304.9±156.3) was significantly higher than the Ac2-26 patch (175.8±42.2, $p<0.05$), nanofibrous patch (153.7±54.8, $P<0.01$), AQUACEL Extra (101.7±29.9, $P<0.001$) and control (103.0±94.0, $P<0.01$) groups. Statistical analysis of total vessels area between groups demonstrated blood vessels maturation during the healing process. In addition, new capillary vessels length density (see SI for details of the measurements) was determined by stereology assessment and the results showed that capillary vessels formation promoted by FSTL-1 and composite patches were remarkably higher than other patches.

Imaging and quantification of numerical density of new capillary vessels of infected diabetic wounds after 7 and 15 days of wound induction showed that the composite patch could induce significantly higher angiogenesis than the other groups. In addition, both the total volume of the vessels and the new capillary vessels length density revealed the exceptional role of the composite patch in efficient development of vessel formation and maturation.

Figure 5A:
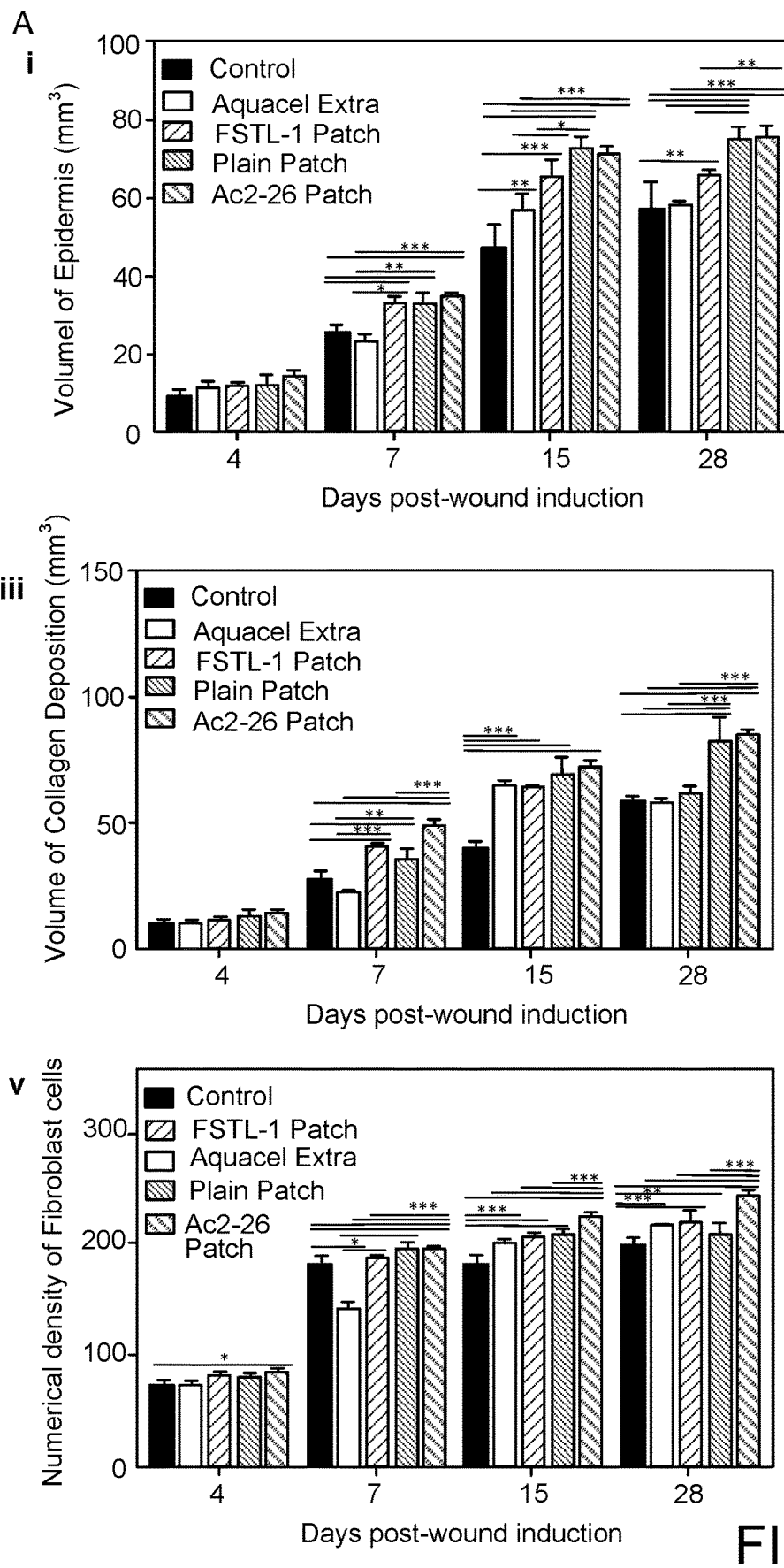
FIGS. 5A and 5B show in vivo results of using the patches in rats.
Figure 5A:
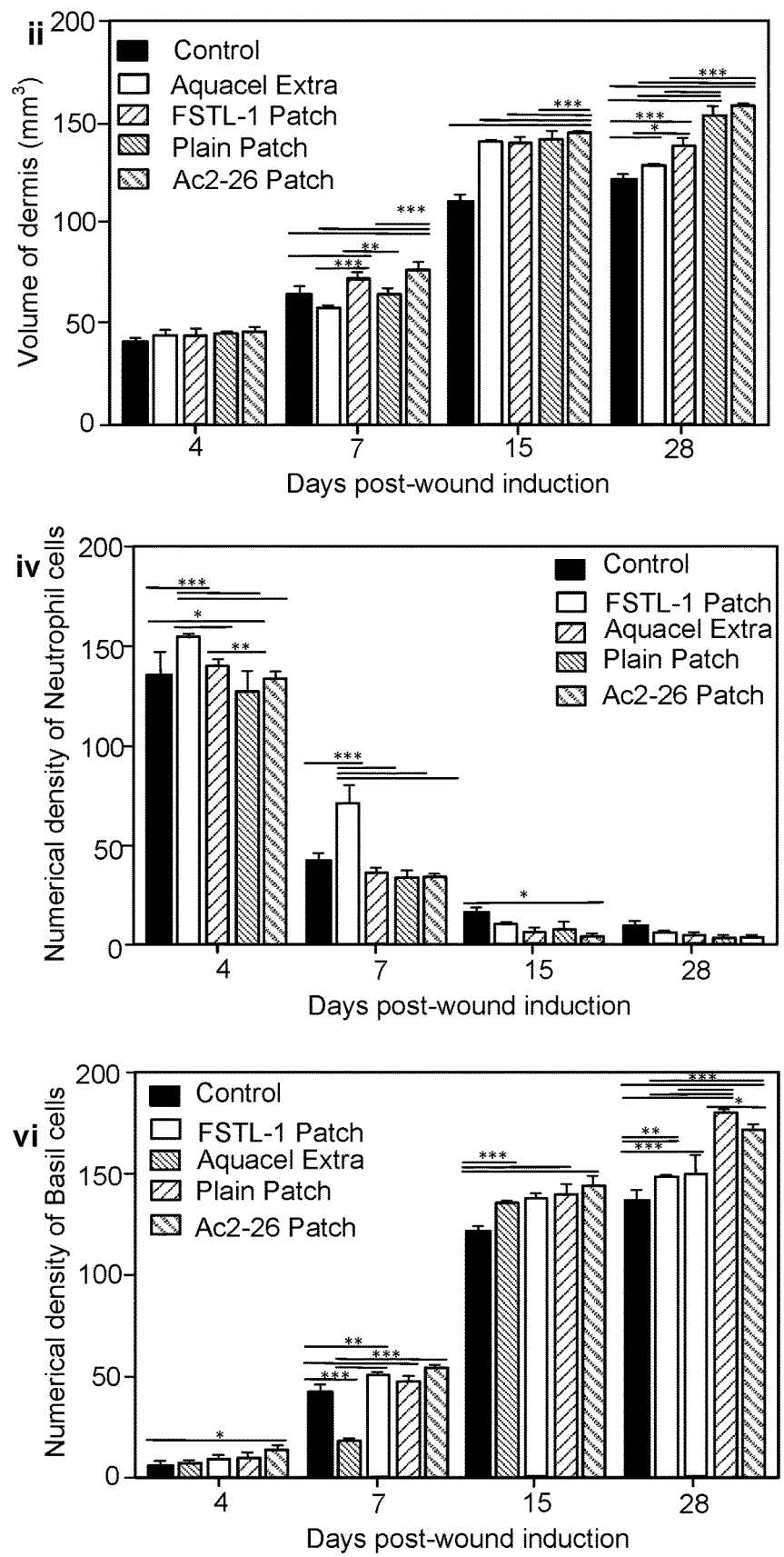
Figure 5B:
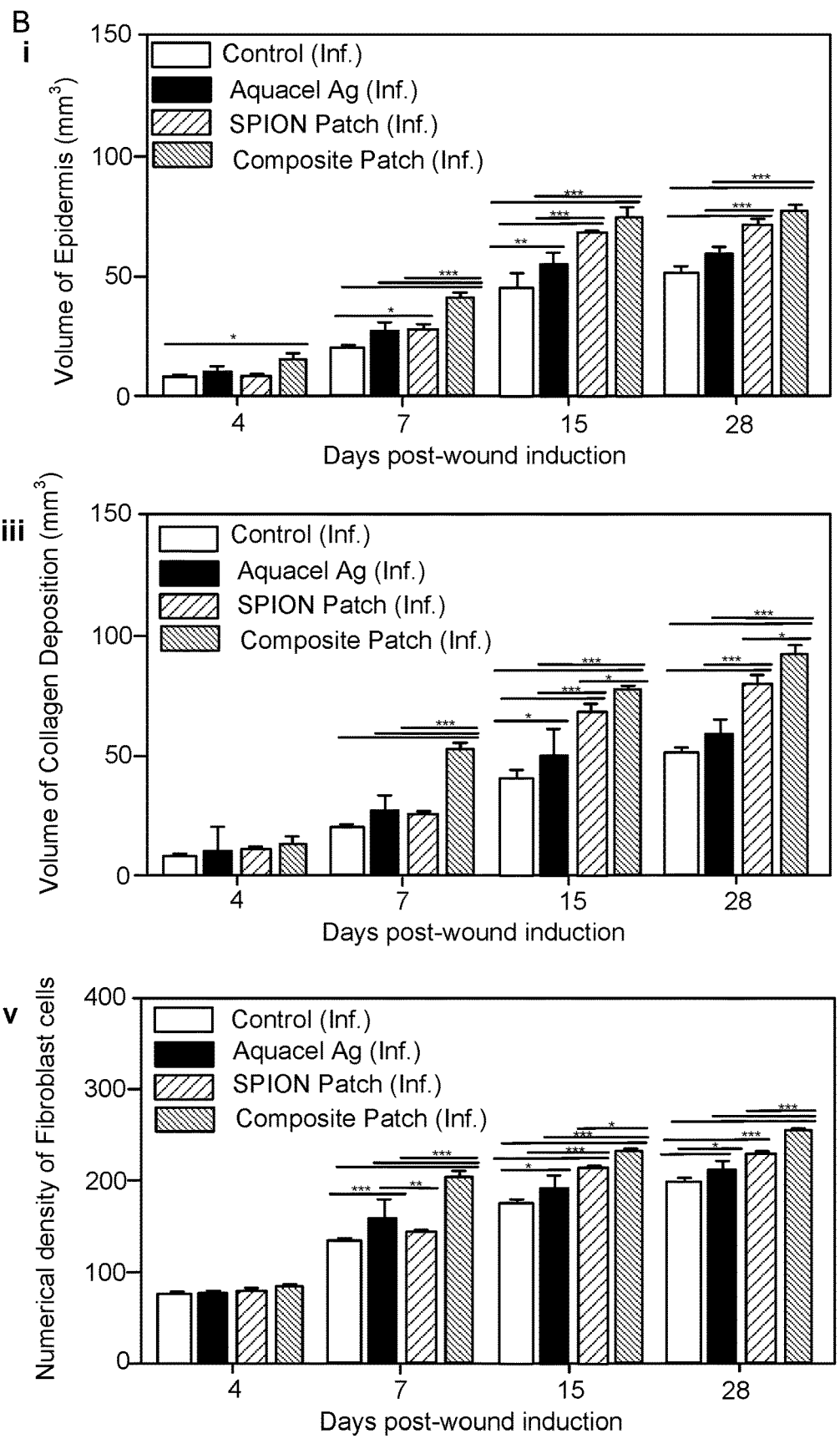
Figure 5B:
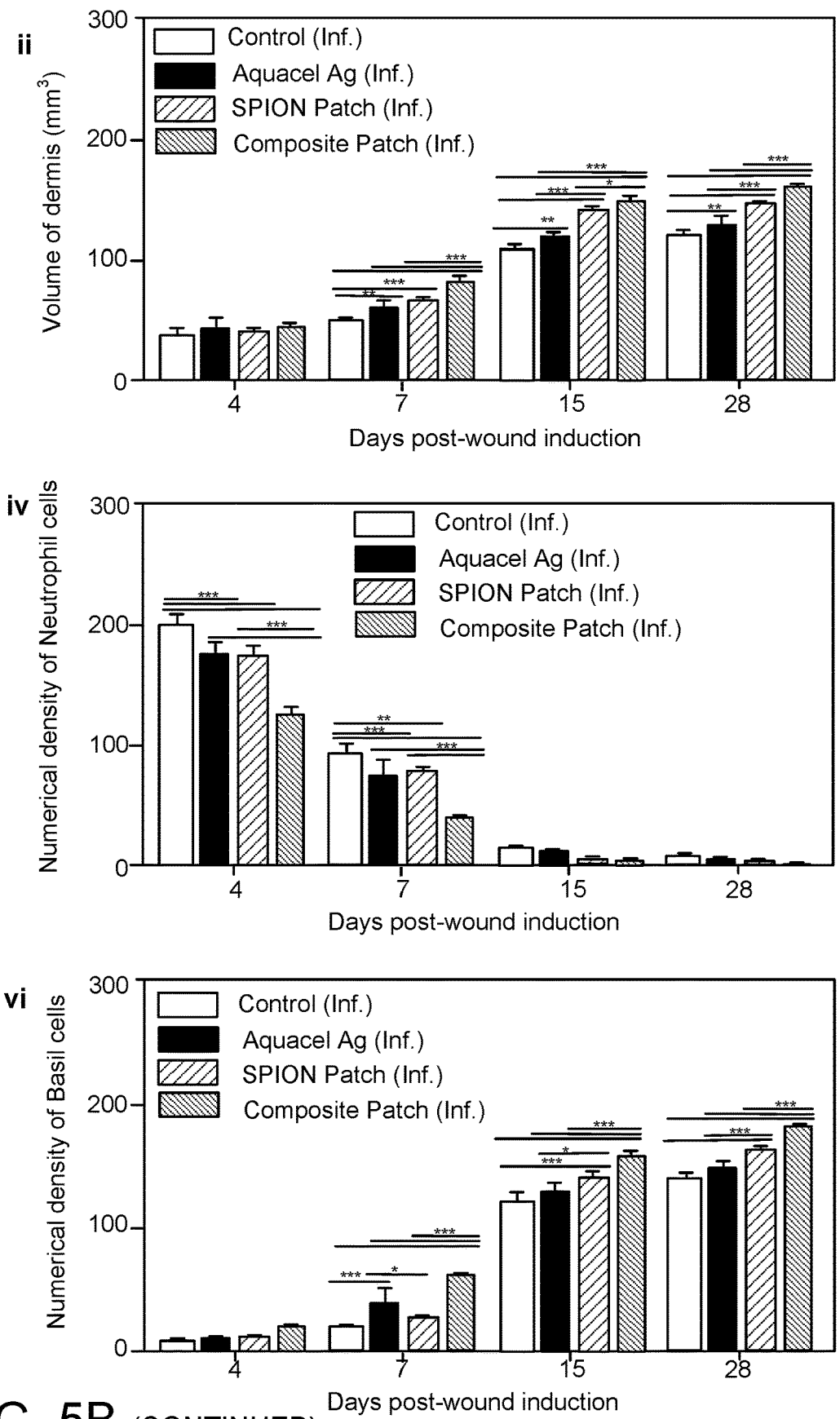

FIGS. 5A and 5B summarize the results of wound healing in diabetic rats. FIG. 5A shows results of diabetic non-infected rats that were treated with a nanofibrous patch, FSTL-1 patch, Ac2-26 patch, AQUACEL Extra®, and control group. FIG. 5B shows diabetic-infected rats (inoculated with *S. Aureus*) that were treated with SPION patch, Composite patch, AQUACEL Ag® during the healing process. Shown are the volume density of the (i) epidermis, (ii) dermis, (iii) collagen bundle deposition, numerical density of (iv) fibroblast cells, (v) neutrophil cells, (vi) basal cells, at the wound site after determined time points of wound induction for control and treatment groups.

Overall, in vivo analysis of the wounds revealed that patches could substantially accelerate both wound closure and regeneration with no sign of scar formation, immunological reaction, or cytotoxicity.

Clinical Studies

The therapeutic wound healing capability of the bioengineered polymeric patches was examined following application to 14 patients with non-healing chronic diabetic wounds who failed the standard of care compression therapy (a simple and effective approach which increases blood flow activity through strengthening vein support) and other available approaches (the use of commercial wound healing products). Informed consent were obtained from all participates in this study, their blood glucose level was controlled and any other required intervention during the study was provided by experienced medical staff. The analysis of clinical data of patients using the nanofibrous patches revealed that the average healing rate was relatively fast (26±18% cm/day).

Figure 6B:
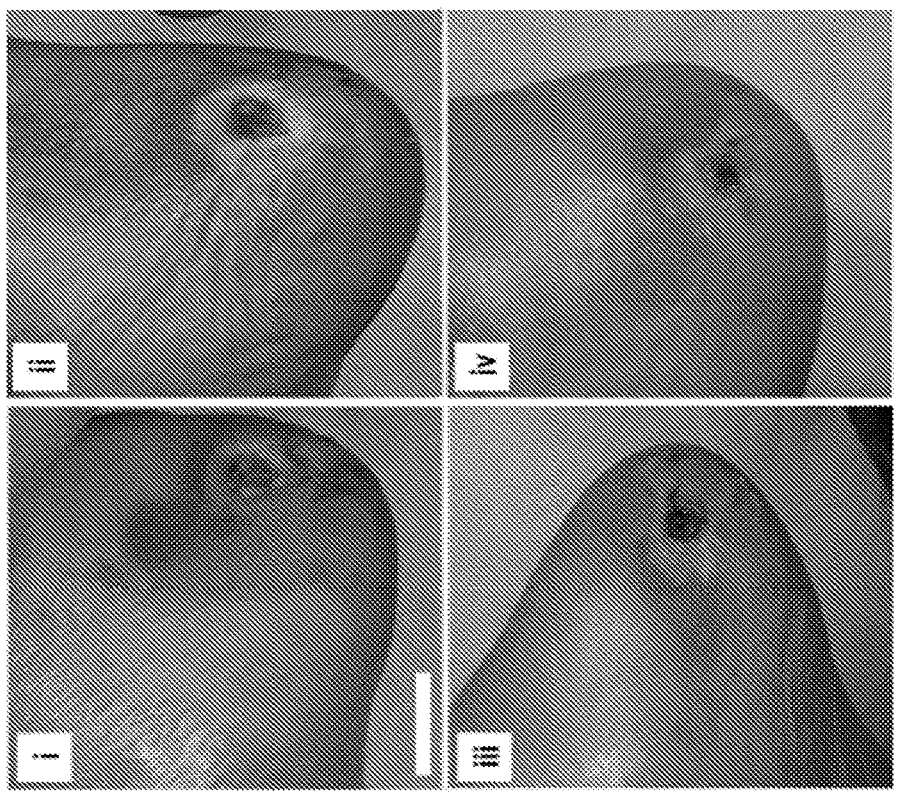
FIGS. 6A and 6B show in vivo results of using the patches in clinical trials.
Figure 6A:
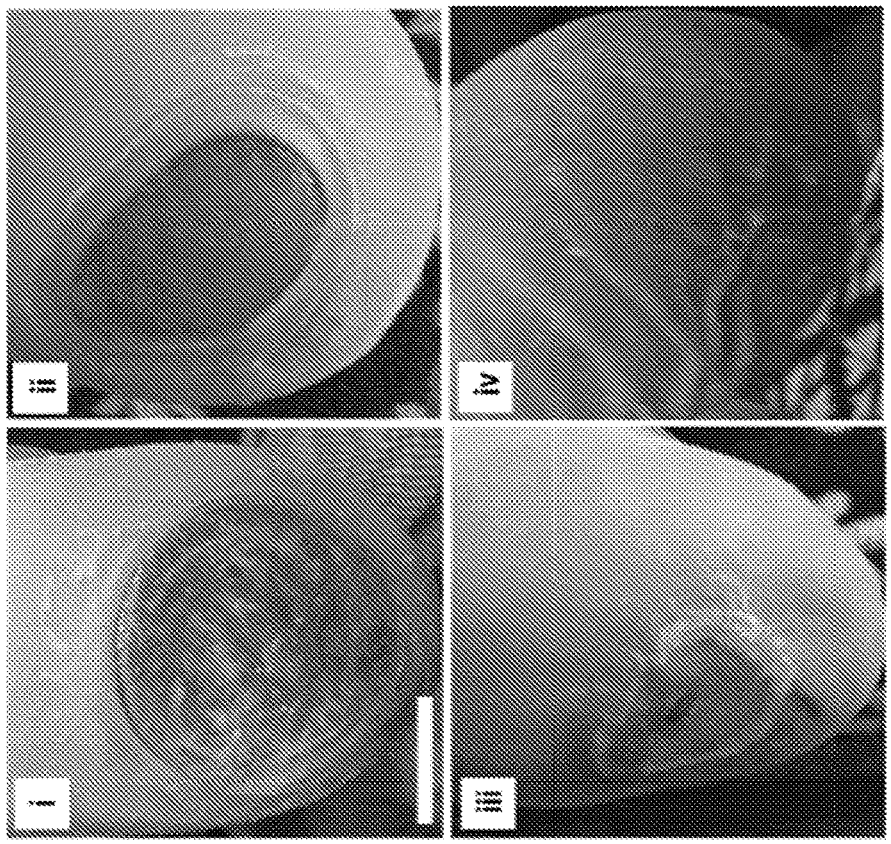

FIGS. 6A and 6B show clinical study results of patients' treatment with the nanofibrous patch. Variations in healing among the patients was observed and was likely related to their health conditions and their wound shape and dimensions; however, the chronic wounds of all 14 enrolled patients healed after treatment with the patches. The healing rate of circle shaped wounds was faster than others with irregular contours. The wounds' size and complication of the patients' disease affected the healing rate and the period of the follow up for each case. Overall, every case was followed up for at least two months.

FIG. 6A represents an example of a 14 weeks old non-healing chronic diabetic wound on the plantar fascia of a 71-year-old male (i) before and after (ii) 3 weeks, (iii) 5 weeks, and (iv) 7 weeks of treatment initiation. The use of the nanofibrous patch could completely heal the wound eight weeks after implantation. The wound surface area was measured by digital planimetry software. In another case study, a 12-week-old non-healing diabetic heel wound of a 49-year-old male was cured in less than 2 weeks after treatment with the patch. FIG. 6B shows at (i) 0, (ii) 10, (iii) 15, and (iv) 20 days of treatment with the nanofibrous patch.

The unique patches described herein enable minimization of the complications caused by bacterial biofilm formation by incorporating immune-activator agents, such as SPION ferumoxytol. The immune activation role of the SPION ferumoxytol was used to inhibit cancer tumor growth. The patches have the distinct capability of these particles to change the functionality of macrophages from M2 to M1 can locally activate the impaired immune system in chronic wounds and at the same time remove pathogenic bacterial colonies. In addition, the formation of a protein corona can substantially enhance i) the ability of SPION ferumoxytol to change the functionality of macrophages from M2 to M1 and ii) the release of beneficial pro-inflammatory cytokines (e.g., TNF-α) during the wound healing process. Following analysis of the role of SPION ferumoxytol and after inducing Fenton reaction which activates macrophages (as SPIONs are physically attached to the fibers and are available to macrophages at the very first stage of interactions between the patch and wound), the integrated pro-resolving mediator Ac2-26 which is embedded in the nanofibrous structure would be available to the activated macrophages during the patch degradation, thus overcoming the complication associated with prolonged inflammation and accelerating the healing process.

To test the role of protein corona (at different protein concentrations) in the polarization of macrophages exposed to the SPION ferumoxytol were incubated for 30 min, and subsequently, their transcriptomes for expression differences of proinflammatory versus anti-inflammatory mRNAs were analyzed via Real-time RT-PCR. This analysis showed that SPION ferumoxytol initially exposed to fetal bovine serum and human serums at 10% and 50%, significantly up-regulated TNF-α, iNOS, and CD86 markers, indicating that the polarization of macrophages to proinflammatory phenotypes (M1) occurs only in serum-containing media. By contrast, mRNA levels of anti-inflammatory CD206, ARG1, and IL10 markers were significantly decreased after exposure to SPION ferumoxytol without protein corona. Similarly, the production of pro-inflammatory cytokines such as TNF-α and Il12p40 significantly increased in the serum containing media, but no significant production of anti-inflammatory cytokines such as IL-10, IL4, and IL13 was observed. The enhanced production of TNF-α has a beneficial role in the wound healing process as it can induce expression of vascular endothelial growth factor A in keratinocytes and fibroblasts. TNF-α can also increase synthesis of a wide range of Metalloproteinases (MMPs) including MMP-1, MMP-2, MMP-3, MMP-9, MMP-13, and MT1-MMP. MMPs have a crucial role in several stages of the wound healing process through facilitating cell migration and tissue remodeling.

The phenotypic heterogeneity of macrophages was also measured by flow cytometry analyses, using a combination of CD80 and CD206 lineage markers. Al macrophage interacting with SPION ferumoxytol in serum-containing media demonstrated significant increase in CD80+CD206− (M1) expression and significant decrease in CD206+CD80− (M2) expression in comparison with control and the serum-free conditions. These results indicate that the absence of serum proteins in the media constitutively limits the SPION ferumoxytol dependent function of macrophages. In other words, the interaction of the SPIONs with the wound exudates and drainage fluid can further help macrophage M1 activations which is beneficial for bacterial removal.

To incorporate SPION ferumoxytol with the bioengineered polymeric scaffolds, the dried scaffolds were immersed in SPIONs ferumoxytol media (concentration of 32 μg/ml) for one hour. It is expected that SPION ferumoxytol is physically incorporated in the scaffolds' nanofiber structures. Gentamicin-susceptible *Staphylococcus aureus* (ATCC 12600) was cultured on the surface of the functionalized patch, in the presence and absence of macrophages, and probed their growing both using live/dead assay and counting the number of bacterial colonies after digestion of the patches. The results confirmed that the percentage of inactive bacteria in the biofilms is significantly (P<0.01; n=8) higher in the presence of macrophages compared to the patch containing SPION ferumoxytol alone.

Owing to its multifunctional capacity, the novel patches introduced here show promising alternative for activating several resumed healing mechanisms in chronic wounds. As it is evident from the in vivo rat experiments and limited human clinical trials, the novel design of the patches can be used as reliable wound healing device for any patient suffering from chronic and diabetic wounds. The efficiency of the proposed patches in promoting and accelerating the healing process of chronic wounds in the diabetic animals and patients is evident.

Figure 7:
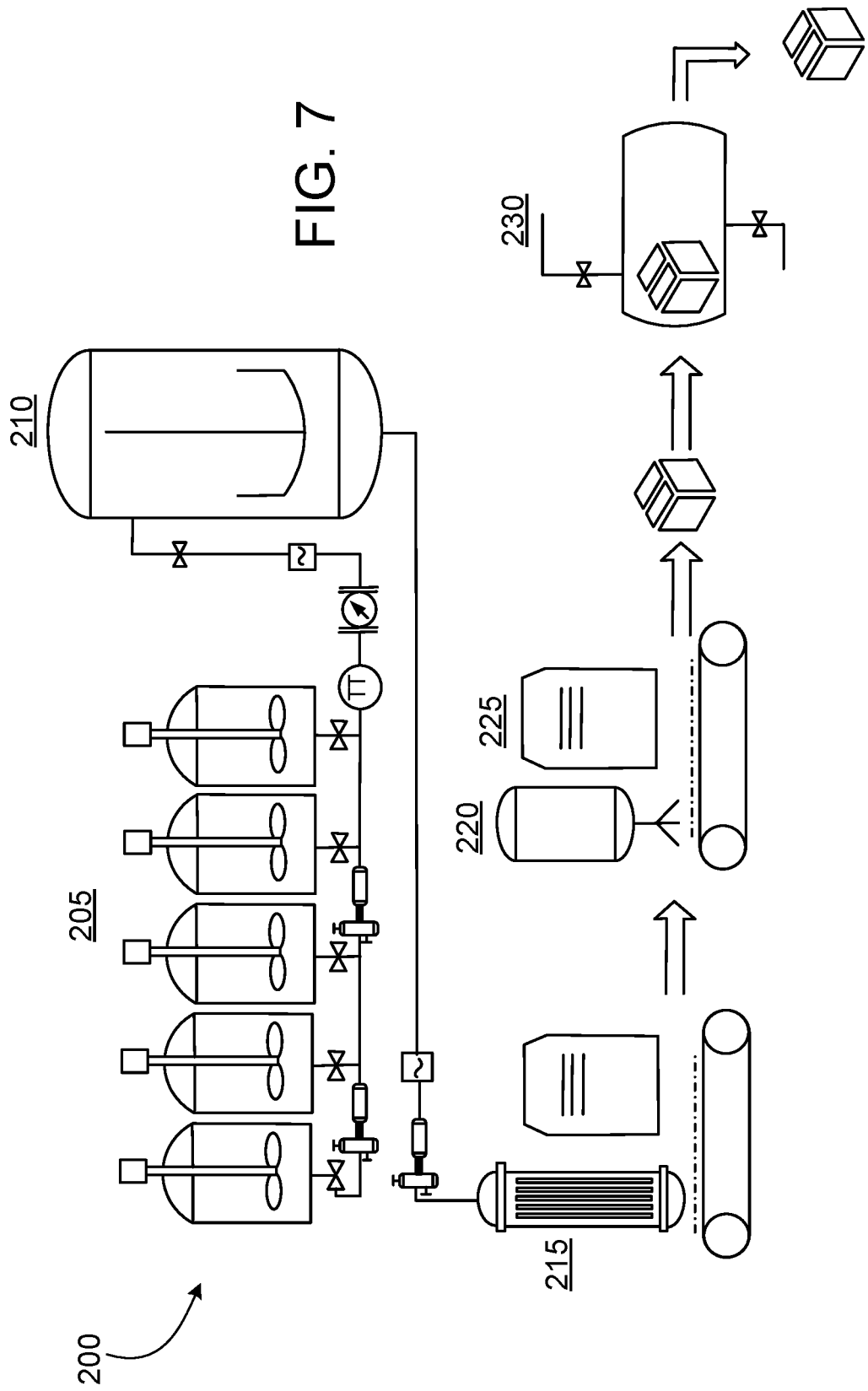
FIG. 7 shows an exemplary manufacturing process for creating skin patches.

FIG. 7 shows an exemplary manufacturing process 200 for creating the patches described herein, scaled up from lab-scale production. The solution-making solutions 205 (collagen I, chitosan, chondroitin sulphate, elastin, hyaluronic) and mixing components solution 210 are available in industrial quantities, e.g., vats. These components are nanoextruded at a large-scale nanoextruder 215. SPION spray is applied from a spray reservoir 220 and the solution dried by a drier 225. The resulting patches are packaged, and sterilized by sterilizers 7. Various conveyors, valves, pump, and sensors can be used, as is known in the art.

A number of embodiments of the invention have been described. Nevertheless, it will be understood that various modifications may be made without departing from the spirit and scope of the invention. For example, although non-extrusion is described, other approaches for production of nanofibers are possible, such as using a high speed spinning disk. Accordingly, other embodiments are within the scope of the following claims.

What is claimed is:

1. A method of fabricating a skin wound patch, the method comprising:
preparing a biopolymeric solution comprising chitosan, collagen, chondroitin sulfate, elastin, hyaluronic acid, follistatin-like 1 (FSTL-1), iron oxide nanoparticles, and AC2-26 peptide;
filtering the biopolymeric solutions through a filter membrane;
extruding the biopolymeric solution through an extrusion device to form a nanofibrous composite;
collecting the extruded nanofibrous composite on a sterilized plate; and
drying the extruded nanofibrous composite into a solid patch.

2. The method of claim 1, wherein the extrusion device comprises a nanoporous membrane.

3. The method of claim 2, wherein the nanoporous membrane has a pore size between 10 nm to 2000 nm.

4. The method of claim 3, further comprising feeding the biopolymeric solution through the nanoporous membrane at a constant flow rate.

5. The method of claim 4, wherein the constant flow rate is between 1-1000 µl/min for a 400 nm pore size membrane.

6. The method of claim 1, wherein drying the extruded nanofibrous composite occurs at temperature between 5° C. and 50° C.

7. The method of claim 6, wherein drying the extruded nanofibrous composite occurs at room temperature.

8. The method of claim 1, wherein drying the extruded nanofibrous composite occurs at atmospheric pressure.

9. The method of claim 1, wherein drying the extruded nanofibrous composite occurs under vacuum.

10. The method of claim 1, further comprising neutralizing the dried patch with neutralizing agents.

11. The method of claim 1, wherein the neutralizing agent is sodium hydroxide.

12. The method of claim 1, comprising sealing the extrusion device with an O-ring.

13. A patch for use in healing chronic skin wounds, the patch comprising:
a scaffold having nanofibers;
FSTL-1 embedded in the nanofibers;
AC2-26 peptide embedded in the nanofibers; and
superparamagnetic iron oxide nanoparticles that are physically attached to the scaffold.

14. The patch of claim 13, wherein the FSTL-1 is homogeneously embedded in the nanofibers.

15. The patch of claim 13, wherein the AC2-26 peptide is homogeneously embedded in the nanofibers.

16. The patch of claim 13, wherein the patch has nanofibers 250-450 nm in diameter.

17. The patch of claim 13, wherein the patch has a maximum stress of about 122.5 kPa at an elongation of about 40%.

18. The patch of claim 13, wherein the patch has an adhesive strength of about 70.6 kPa and elastic modulus of about 585.3 kPa.

19. A method of treating a chronic skin wound in a subject in need thereof comprising applying the patch of claim 13 into the subject.

* * * * *

UNITED STATES PATENT AND TRADEMARK OFFICE
CERTIFICATE OF CORRECTION

Page 1 of 1

PATENT NO. : 11,406,740 B2
APPLICATION NO. : 17/055786
DATED : August 9, 2022
INVENTOR(S) : Mahmoudi It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 79 days.

Signed and Sealed this
Eleventh Day of February, 2025

Coke Morgan Stewart
*Acting Director of the United States Patent and Trademark Office*